United States Patent [19]
Hetrick

[11] Patent Number: 5,389,224
[45] Date of Patent: Feb. 14, 1995

[54] CAPACITIVE A/F SENSOR

[75] Inventor: Robert E. Hetrick, Dearborn Heights, Mich.

[73] Assignee: Ford Motor Company, Dearborn, Mich.

[21] Appl. No.: 84,498

[22] Filed: Jul. 1, 1993

[51] Int. Cl.$^6$ .................................... G01N 27/26
[52] U.S. Cl. .................... 204/425; 204/426; 204/427; 324/470; 123/438
[58] Field of Search .............. 204/424, 425, 426, 427, 204/153.18; 324/470, 33; 123/438

[56] References Cited

U.S. PATENT DOCUMENTS

| | | | |
|---|---|---|---|
| 4,272,329 | 6/1981 | Hetrick | 204/406 |
| 4,381,224 | 4/1983 | Fate | 204/406 |
| 4,629,549 | 12/1986 | Kojima | 204/406 |
| 4,729,824 | 3/1988 | Giner | 204/415 |
| 4,841,934 | 6/1989 | Logothetis | 204/406 |
| 4,900,405 | 2/1990 | Otagawa | 204/412 |
| 4,935,119 | 6/1990 | Yamada | 204/425 |
| 5,032,248 | 7/1991 | Kanamaru | 204/425 |
| 5,106,480 | 4/1992 | Croset | 204/424 |
| 5,275,712 | 1/1994 | Hetrick et al. | 204/425 |

OTHER PUBLICATIONS

SAE Paper 860409 Wide-Range Aù-Fuel Ratio Sensor (Feb. 1986).

*Primary Examiner*—John Niebling
*Assistant Examiner*—Bruce F. Bell
*Attorney, Agent, or Firm*—Peter Abolins; Roger L. May

[57] ABSTRACT

A sensor for determining the stoichiometric air to fuel ratio (A/F) at the intake of an internal combustion engine is based on a capacitive device in the exhaust stream which can be used to measure the change in the workfunction of an appropriate material which occurs at the stoichiometric point and which forms one of the two interacting elements of the capacitor. To measure A/F over an extended range about stoichiometry the material whose workfunction changes is made the working electrode of an oxygen concentration cell using a solid electrolyte. Oxygen pumping to and from that surface can change the magnitude of the workfunction allowing for a feedback control method for keeping the workfunction constant despite changes in the A/F so that the required pump current becomes a measure of the A/F.

16 Claims, 4 Drawing Sheets

Ip = CURRENT (PUMPING) TO KEEP DEMODULATED CURRENT AT MIDPOINT VALVUE

CAPACITIVE A/F SENSOR

BACKGROUND OF THE INVENTION

1. Field of the Invention

This invention relates to an electrical means to measure the ratio of the concentrations of oxidizing gaseous species to the concentrations of the various reducing gaseous species such as hydrocarbons, hydrogen and carbon monoxide as might be found in the automotive exhaust.

2. Prior Art

It is often desirable to keep the A/F (the ratio of the mass of air to the mass of fuel) at the input to the cylinders of an internal combustion engine near a stoichiometric value. At this value some exhaust emissions are minimized because there is just enough oxygen present to react with all of the injected hydrocarbons.

To maintain A/F control over the life of the car, widespread use has been made of feedback control methods using exhaust gas A/F sensors as the feedback element. These high temperature solid state devices detect various aspects of the ratio of the concentrations of oxidizing species (mostly oxygen) and reducing species (a mixture of hydrocarbons, hydrogen and carbon monoxide) in the automotive exhaust. Under steady state conditions these aspects are proportional to comparable aspects of the A/F at the input to the cylinders.

Stoichiometric A/F sensors have a step-like transfer function in which high/low output is obtained when the ambient gas is, for example, rich/lean of stoichiometry. A very sharp transition between the extreme outputs occurs in a narrow A/F region around stoichiometry thereby sensing that A/F value. Variations in the output in the regions rich or lean of stoichiometry are generally quite small. These sensors are fabricated from oxide materials and typically employ either an electrochemical or resistive mechanism. For example, the oxygen ion conducting $ZrO_2$ doped with $Y_2O_3$ is the solid electrolyte used in combination with catalytically active Pt electrodes in most electrochemical devices. Porous $TiO_2$ doped with fine grains of Pt particles is frequently used for the resistive devices.

In appropriate circumstances it is desirable to operate rich (excess fuel) or lean (excess air) of the stoichiometric A/F. Rich conditions may be required for cold start and high load. Lean conditions favor fuel economy. To obtain the advantages of feedback control under various circumstances, it is desirable to have a wide-range A/F sensor. There are known a variety of electrochemical structures made from the $ZrO_2$ which combine the processes of oxygen pumping and emf measurements using the oxide cells to obtain a wide range of A/F measurements both rich and lean of stoichiometry with a near linear transfer function. See, for example, those described in U.S. Pat. No. 4,272,329 to Hetrick or a publication by Ueno et al. in "Wide-Range Air-Fuel Ratio Sensor" in SAE Paper No. 860409.

SUMMARY OF THE INVENTION

This invention includes device structures and methods of operation which accomplish either stoichiometric or wide-range A/F sensing in a gaseous ambient containing oxygen and reducing species. For the stoichiometric measurement the invention teaches capacitive structures and electrical methods of operation of these structures. The purpose of the electrical method is to measure changes in the workfunction of an appropriate solid surface which is simultaneously one of the surfaces that is part of the capacitive structure. That surface whose workfunction is measured is also one on which the oxidizing and reducing species of the gas phase in question are catalytically reacted.

In the process of interacting with the gas phase species, the surface adsorbs oxygen in such a way that under lean condition (conditions in which oxygen is in excess of the stoichiometric value with respect to the reducing species) the workfunction of the surface increases due to the adsorption process. On passing to rich conditions (conditions in which the reducing species are in the excess of the stoichiometric value with respect to the oxidizing species) those reducing-species react with the adsorbed oxygen thereby removing them from the surface and concomitantly causing a reduction of the workfunction.

For the appropriate surface, this process of oxygen adsorption in the lean environment and oxygen reaction in the rich environment occurs rapidly and reversibly on alternatively passing from rich to lean conditions with the attendant change in workfunction occurring at the stoichiometric ratio thereby sensing that ratio. At the same time the opposing surfaces or electrodes in the capacitive structure are preferably ones whose workfunctions do not change or change weakly with variations of the A/F so that no electrical changes occur in the capacitive devices due to these opposing surfaces which could cancel those effects of the active surfaces. The change in workfunction can be measured by various capacitive methods to provide a useful output for feedback control purposes.

To measure a wide range of A/F, the active surface discussed above is made the working electrode (as opposed to the reference electrode) of an electrochemical cell which employs an oxygen ion conducting solid electrolyte. Then oxygen can be electrochemically pumped to or from the electrode surface by passing current in the appropriate direction through the cell. It has been found that as a result of this pumping, the workfunction of the appropriate active surface can be changed. In an oxidizing ambient, pumping oxygen away from the exposed electrode can reduce the workfunction, while pumping oxygen to the active surface exposed to a reducing gas can increase the workfunction.

A feedback electrical method can be used to pump oxygen to or from the surface in question in just the right amount to keep the workfunction of the active surface, as measured by the capacitive methods, midway between its lean and rich values. The more one is lean (rich) of stoichiometry the more oxygen one must pump away from (toward) the active surface to achieve the intermediate value of workfunction. In this way the magnitude and direction of the electrochemical pumping current required to maintain the workfunction at a value intermediate between its rich and lean extremes becomes a measure of the A/F.

DETAILED DESCRIPTION OF THE INVENTION

In accordance with an embodiment of this invention, a surface sensitive device interacts with an adjacent gas phase to change its properties in such a way as to sense the transition from an oxidizing to a reducing condition in the exhaust gas of an automotive. The device has a step-like change in its output at the stoichiometric ratio of the oxidizing and reducing species and would conventionally be called a stoichiometric A/F sensor. The principle of operation of the device is based on the systematic and reversible change in the workfunction, $\phi$, of a suitable material (e.g. Pt) as its surface is alternately exposed to oxidizing and reducing gaseous conditions.

Figure 1A:
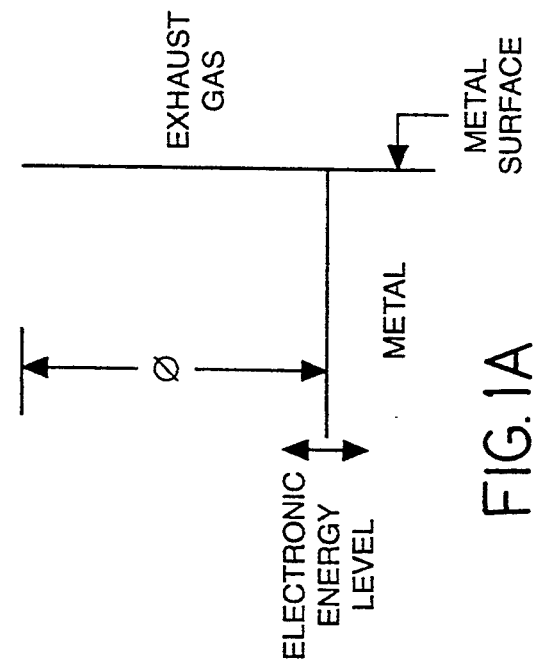
FIG. 1a is schematic electron energy level diagram showing the workfunction $\phi$, of the active sensor surface without adsorbed oxygen. The workfunction is an energy required to remove the least tightly bound electron, whose energy level is represented by the lower horizontal line, to the vacuum level represented by the upper horizontal line.

The horizontal lines of FIG. 1a depict the electron energy levels in a metal with the workfunction being the energy required to remove the least tightly bound electrons in the solid (represented by the lower horizontal line) to a vacuum level (represented by the upper horizontal line). The surface of the crystal is represented by the vertical line. The value of the workfunction can range from about 5.0 eV for some metals such as Pt to values on the order of 3.0 eV for the alkali metals. For nonmetallic materials the workfunction can be much larger.

When some metals are exposed to gaseous oxygen, the oxygen molecules will adsorb on the surface thereby affecting the workfunction. The mechanism for this is one in which the adsorbed O atom being very electronegative, attracts metal electrons to itself leaving behind a compensating positive charge in the metal. The result is a formation of an electrical double layer of charge at the surface which acts to increase the workfunction. The magnitude of the increase can be as large as 1 eV, a substantial percentage change. If these surface oxygen atoms are removed, for example by reaction with other gaseous species such as hydrocarbons or other oxidizable species then the workfunction would return to its previous smaller value.

For an appropriate metal surface, the reaction of reducing and oxidizing species is rapid as would be the case for a catalytic surface. For this circumstance the change in the workfunction would occur abruptly and quickly at the stoichiometric ratio without hysteresis or time delays. Platinum is an especially appropriate surface material since only very thin oxide coatings (perhaps as small as a monolayer) are formed and these are easily and quickly removed at moderately elevated temperatures (>300° C.) in a reducing atmosphere such as would be found in an automotive exhaust under rich conditions. For Pt the increase in workfunction on passing from rich to lean gaseous conditions is about 0.7 eV.

A sensor of the stoichiometric ratio, in accordance with an embodiment of this invention, uses an electrical method for reading out the change in workfunction. There are a number of capacitive structures and associated electrical methods which could accomplish this. These devices are based on the fact that when the workfunction changes for either of two materials which form a structure with mutual capacitance, and if those two materials are electrically connected, a current will flow between the materials whose integrated amount will increase with the capacitance and with the change in the workfunction. A circuit which measures this total current flow thus measures the change in workfunction and for the circumstances under consideration, the stoichiometric A/F.

The reason for the current flow is to maintain the equilibrium between the electrons of one material and the electrons of the other. Thus, if the workfunction of one material increases, all of its electrons are moved to a lower energy level relative to those of a material whose workfunction does not change. If the materials are connected electrons will flow from the latter to the former material as they seek out lower energy levels.

Thus, a current flows between the two materials for a finite time because the continued transfer of electrons builds the negative electrostatic potential of the receiving material at the expense of the transmitting-material. These changes in potential are of such a sign to establish the equality between the energy levels of the electrons in each material so that the current flow eventually stops.

Figure 2A:
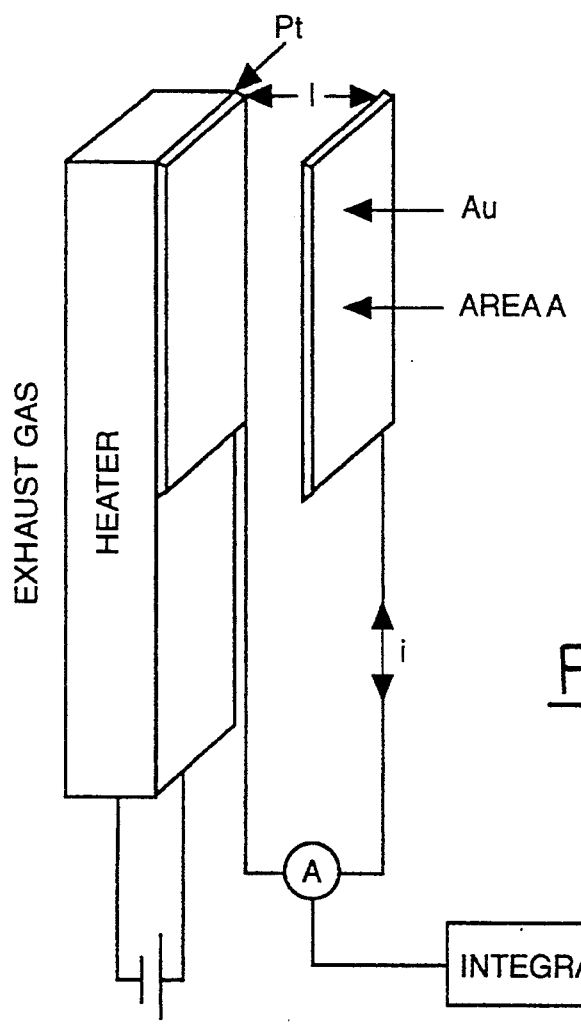
FIG. 2a is one embodiment of a capacitive A/F sensing structure in which a thin rectangular sheet of Pt resting on a heater, which elevates the temperature to the range of 500° C. and exposed to the exhaust gas, is placed at a distance 1 from a thin rectangular, and chemically inactive, gold layer to form the two plates of a parallel plate capacitor. The plates are connected by an ammeter and an attached current integrator.

A first embodiment of a capacitive structure is shown in FIG. 2a in which a structure 20 includes a plate of Pt, held at an elevated temperature (e.g. 500° C.) by an attached heater, placed in the exhaust gas, and positioned a distance l away from a chemically inert electrode such as Au (gold) to form a parallel plate capacitor structure with capacitance $C = \epsilon A/l$ where $\epsilon$ is the dielectric constant of the atmosphere between the plates, and a is the area of the identical plates. Other capacitive structures may be chosen with attendant changes in the geometric factors defining the capacitance. The use of Au as the opposing electrode is advantageous since its workfunction does not change significantly when exposed to the various conditions of the exhaust atmosphere. The current flow between the two plates due to gas induced changes in the Pt workfunction, is detected by an ammeter A. The instantaneous magnitude of the current i is given by equation 1 where $Q = C\Delta\phi$ is the instantaneous charge stored on each plate corresponding to a given C and $\Delta\phi$, which is difference in workfunctions between Pt and Au.

$$i = dQ/dt = C(d\Delta\phi/dt) = (\epsilon A/l) \, d\Delta\phi/dt \quad (1)$$

The formula for the parallel plate capacitor indicates the appropriate parameters to vary to achieve the largest and most easily measurable current. Since the gas flow rate past the sensor may vary leading to different magnitudes of the current, it may be more beneficial to measure the integrated current flow with an integrating circuit attached to the ammeter.

Figure 2B:
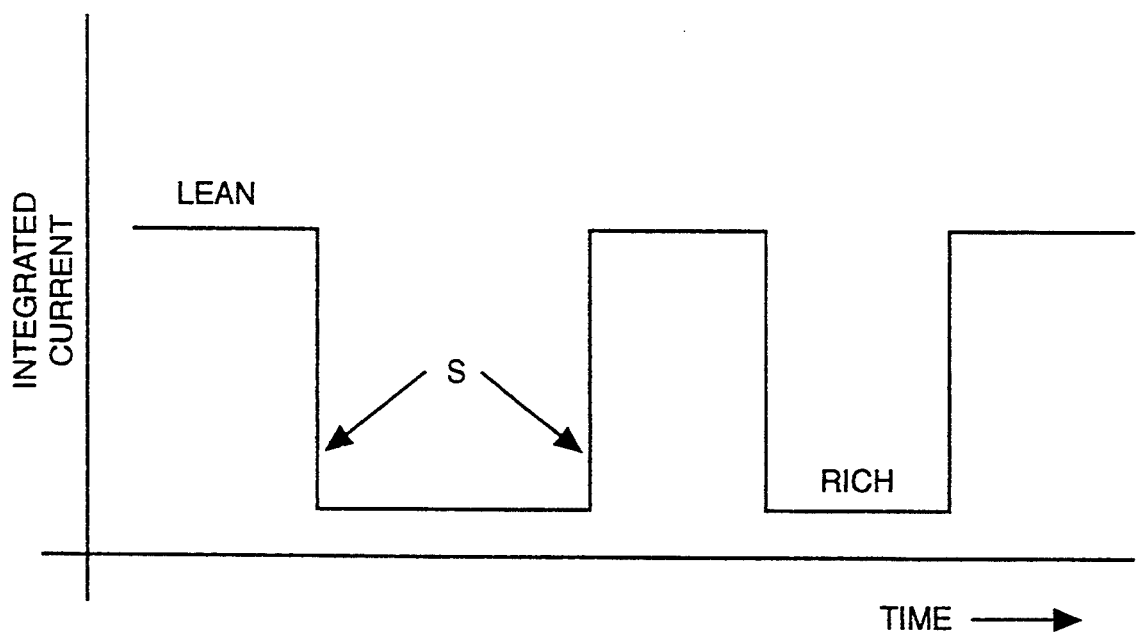
FIG. 2b is a schematic diagram of the square wave output of the integrator that results when the exhaust gas is alternatively switched from lean to rich air-fuel conditions. The position of the switch occurs at the stoichiometric A/F and results from the removal or accumulation of adsorbed oxygen which occurs on the Pt at the ratio.

FIG. 2b shows a schematic diagram of the step-like output versus time from such a sensor as the exhaust gas varies alternately from rich to lean conditions. As long as the capacitance does not change, the total charge transferred between plates will remain constant with each traverse through stoichiometry. Using this integrator output, well known circuits could be attached to the integrator to effect the feedback control of A/F.

Figure 3A:
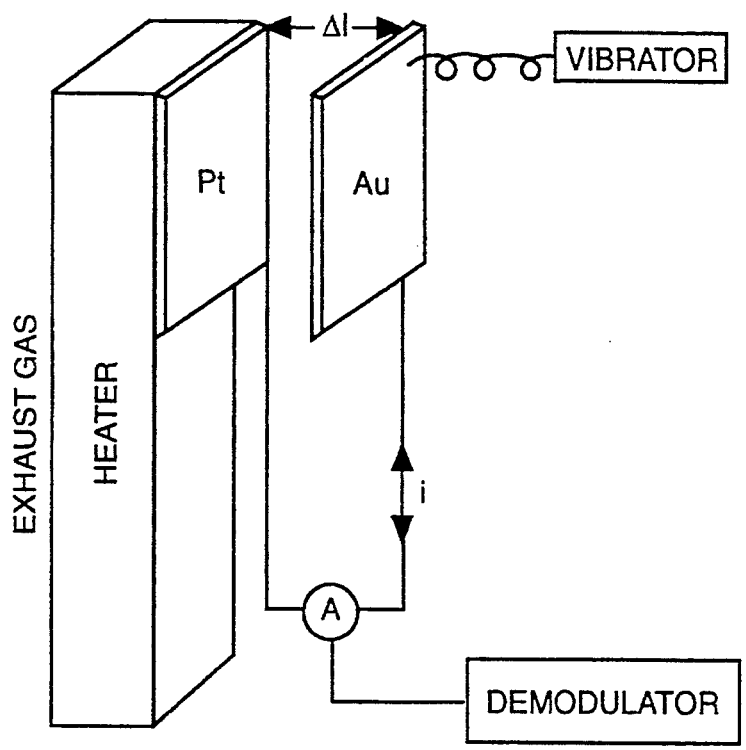
FIG. 3a is a second embodiment of a capacitive A/F sensing structure in which Pt and chemically inactive surfaces (such as gold) are caused to vibrate a distance 1 with respect to each other at a frequency f. Because of the difference in workfunction between the materials this vibration causes an ac current to flow at the frequency f. This alternating current can be demodulated for convenient feedback control purposes.
Figure 3B:
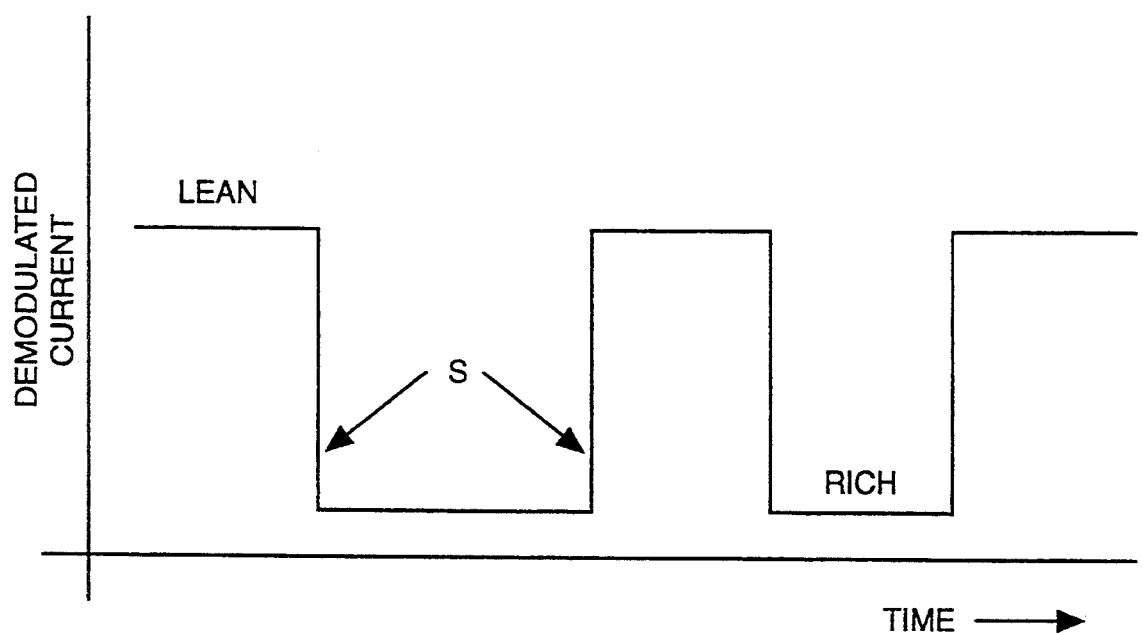
FIG. 3b is a schematic diagram of the demodulated current which changes reversibly in a step-like manner at the stoichiometric ratio when the A/F is varied from rich to lean conditions.

An alternative mechanism for measuring the change in workfunction and the corresponding A/F transition is to adapt the "Kelvin method" fully described in Chapter 3 of "Experimental Methods of Catalytic Research" Edited by R. B. Anderson, Academic Press, New York, 1968, the disclosure of which is incorporated herein by reference. In this method as illustrated in FIG. 3a, the Au or chemically inactive electrode is caused to vibrate sinusoidally at a frequency f (either or both electrodes could participate in the vibration). Using the same formula for the charge and the capacity of a parallel plate capacitor as above, the current flowing as a result of the Vibration is given by $$i = i_o \cos(2\pi ft) = \epsilon A \, (\Delta l/l^2) \, \Delta\phi \cos(2\pi ft) \quad (2)$$

where $i_o$ is due to the change in separation $\Delta l$ between the two plates. This ac signal can then be demodulated to give an output proportional to $\Delta\phi$. When $\Delta\phi$ changes, the demodulated signal will change in a well defined way as shown in FIG. 3b. This method has the advantage of ac operation so that narrow-band detection can be used to eliminate noise. A number of methods including piezoelectric, electromagnetic, etc. may be used to effect the vibration. If the desired response time for a sensor is $\tau$, then one must operate at a frequency where $\tau > 1/f$ to allow a number of vibrational cycles to occur during the change in $\Delta\phi$.

Figure 4A:
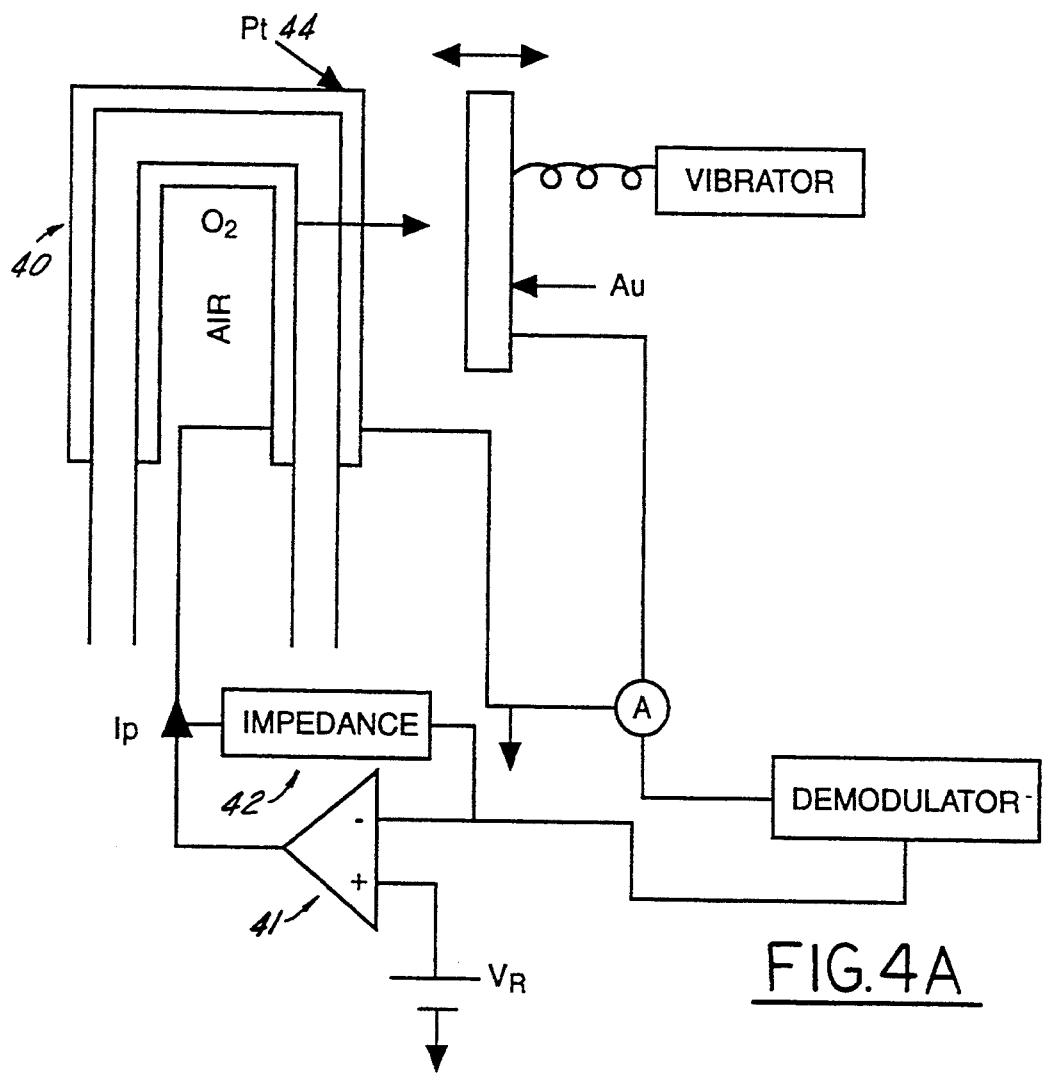
FIG. 4a is a schematic diagram of a wide range A/F sensor in which an oxygen-ion conducting, solid electrochemical cell in the form of a cylinder closed at one end with inner and outer Pt electrodes is placed in proximity to a vibrating gold surface. The outer, active Pt surface is exposed to the exhaust gas while the inner surface is exposed to an air reference atmosphere. The demodulated output of the ammeter placed between the two capacitive surfaces forms one input of a negative feedback surface designed to keep the workfunction at a fixed value intermediate (and represented by the voltage $V_R$) between those of the rich and lean extremes. The output of the circuit is a current $I_p$ which causes oxygen to be pumped in the electrochemical cell.

Either of the two capacitive methods described above can be modified to allow for an extended range of A/F sensing around stoichiometry by using oxygen pumping techniques combined with some special properties of Pt. FIG. 4a illustrates how this is accomplished in an electrochemical cell 40 in which a Pt plate 44 has been modified to become the outer, working electrode of a high temperature, solid state oxygen concentration cell. The working electrode is exposed to the exhaust gas rather than the reference electrode which is exposed to a reference atmosphere which is usually air in the automotive application. A well known technology for doing this involves the use of ceramic electrolytes made from oxygen ion conducting $ZrO_2$ doped with $Y_2O_3$. An appropriate geometry for the automotive application is one in which the electrolyte is shaped in the form of a cylinder with one end closed and with both the inner and outer surface coated with porous Pt electrodes. Such electrodes facilitate the operation of the cell by catalyzing the uptake of oxygen from the gas phase and the incorporation of the oxygen into the electrolyte. When a potential difference is applied between the two electrodes, oxygen in the gas phase adjacent to the more negative electrode is caused to be pumped through the electrolyte to the gas phase adjacent to the opposite electrode. That is, when making a wide range A/F measurement note that oxygen pumping changes the workfunction of the Pt electrodes. Thus pumping oxygen to the working electrode causes the workfunction to increase while pumping oxygen away from the working electrode causes the workfunction to decrease. These general observations are consistent with the gas phase results that an oxygen excess atmosphere causes an increase in the workfunction while a rich or oxygen deficit atmosphere causes a decrease in the workfunction.

Figure 1B:
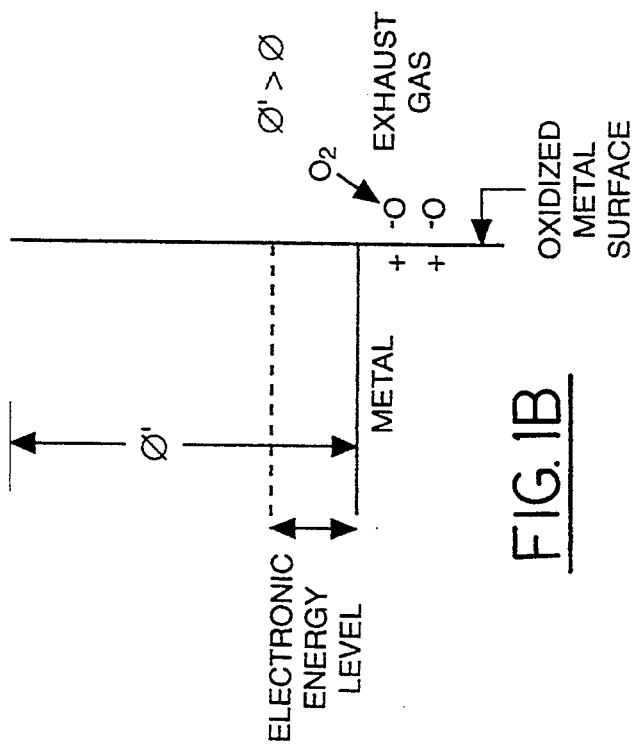
FIG. 1b is a schematic energy level diagram showing the increase in workfunction of the active surface to a new value $\phi'>\phi$ due to adsorption of oxygen on the surface as occurs for Pt and many other metals. The strongly electronegative oxygen atoms attract metal electrons to themselves leaving behind a positively charged region just inside the metal surface. This double layer of charge across the surface causes the increase in $\phi$.
Figure 5:
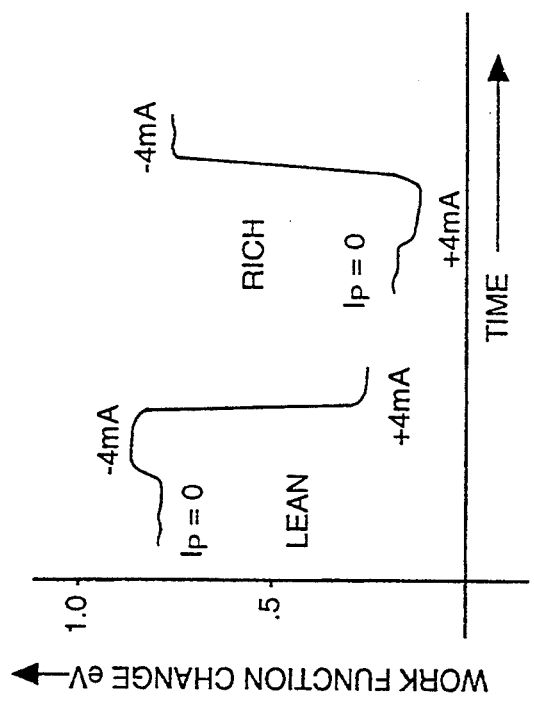
FIG. 5 is a graphical representation of the variation in a Pt electrode workfunction due to the electrochemical pumping of oxygen under both lean and rich conditions as set by mixtures of oxygen and propane.

The results indicated in FIG. 5 show the workfunction change due to oxygen pumping when the gas phase is alternately rich or lean of stoichiometry. When the ambient gas is lean, pumping oxygen to the exhaust gas exposed electrode (corresponding to a −4 mA pump current) increased the workfunction of the Pt. Pumping oxygen away from the surface with the same magnitude of current however caused a decrease in the workfunction by as much as 0.6 eV. This change is close to as much change as occurs due to changing the exhaust gas from a lean to a rich condition. Accordingly, despite the lean gas phase, oxygen pumping of the correct sign and magnitude can modify the workfunction to a value corresponding to a rich or at least an intermediate A/F condition.

Also shown in FIG. 5 is a case where the gas phase is rich for no pump current ($I_p = 0$) corresponding to a low workfunction. Then pumping oxygen away from the surface (corresponding to a 4 mA pump current) serves to reduce the workfunction a little further while pumping oxygen to the surface serves to raise the workfunction by as much as 0.7 eV. Again this change is as much as that which occurs due a change from rich to lean conditions. Thus, oxygen pumping has enough range of authority to modify the workfunction to a value corresponding to a lean condition. Accordingly, the oxygen pumping effect on the workfunction can be used to establish a negative feedback device for sensing a wide range of A/F in a "null method". In such a method the pumping current is applied in an amount to null out the effect of the gas phase and maintain the workfunction at a constant value so that the magnitude of the required pump current becomes proportional to A/F.

Taking the example of the Kelvin method approach illustrated in FIG. 4a, the device is calibrated by determining the dc voltages at the output of the demodulator which correspond to rich and lean conditions. One then chooses a reference value corresponding to a voltage $V_r$ which lies midway between these voltages. One then uses well known methods of negative feedback circuitry in which the reference voltage and the output of the demodulator are input in the manner of negative feedback to an amplifier 41 with feedback impedance, 42. The output of the amplifier is then applied to one of the electrodes of electrochemical cell 40 to cause oxygen to be pumped through the cell. The oxygen is pumped in such a direction and of such a magnitude that the modification to the workfunction described above that results from the pumping offsets the modification that occurs due to a change in the composition of the gas phase so that the workfunction is in fact kept at the intermediate value that corresponds to the reference voltage $V_R$.

Figure 4B:
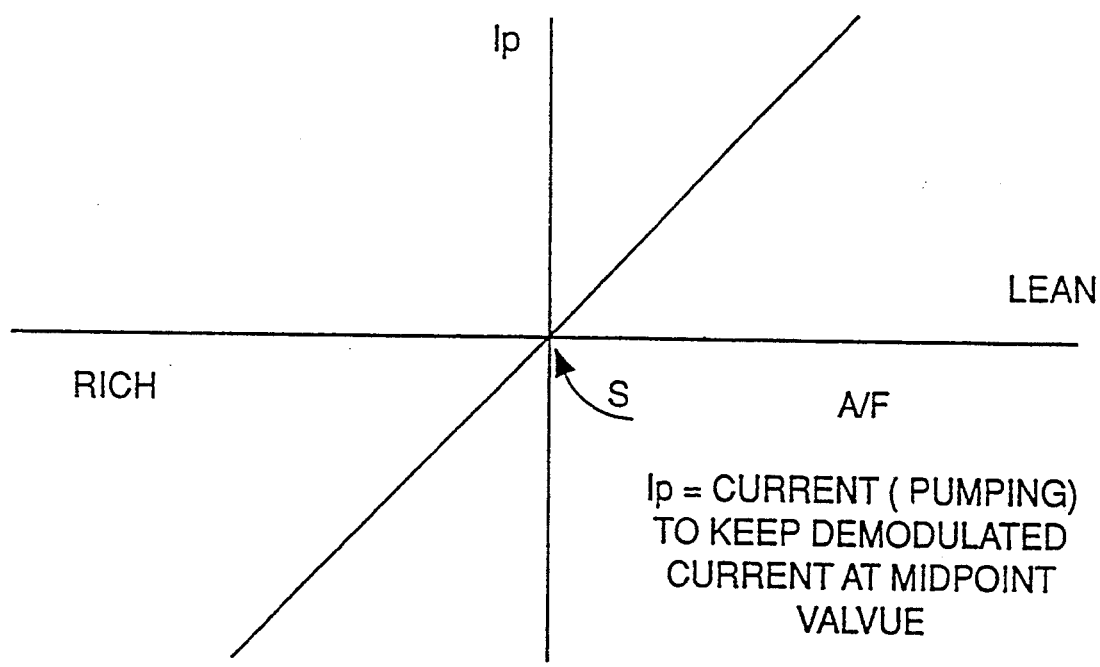
FIG. 4b is a schematic diagram of an output current $I_p$ of the cell which is just adequate to maintain the workfunction of the Pt at a fixed value despite changing A/F conditions in the exhaust gas and thus forms a measure of the A/F over a wide-range of values.

Thus, under lean conditions one must pump oxygen away from the active surface to the reference electrode in order to reduce the workfunction while under rich conditions pumping currents of the opposite sign must be used. The further one is from stoichiometry in either the rich or lean direction the more pumping current will be required to establish the intermediate workfunction value. FIG. 4b shows an example of the linear transfer function that would be expected relating pumping current and A/F. In such a scheme, no pump current would be required at stoichiometry.

Various modifications and variations will no doubt occur to those skilled in the various arts to which this invention pertains. For example, the ceramic electrochemical cell need not be cylindrical but could have a planar geometry. These and all other variations which basically rely on the teachings through which this disclosure has advanced the state of the art are properly considered within the scope of this invention.

What is claimed:

1. A sensing structure for electrically sensing stoichiometric ratio of an oxidizing and reducing species in an ambient gas phase including:
   a material with an active surface which interacts with the gas phase; and
   a capacitive device having plates which are vibrated relative to each other, said capacitive device providing an electrical signal that is proportional to the change in workfunction thereby sensing the stoichiometric ratio.

2. A sensing structure as recited in claim 1 in which said active surface has a catalytic surface characteristic with respect to a reaction of the oxidizing and reducing species, adsorbs oxygen in such a way that the workfunction of the active surface material is increased as a result of such oxygen adsorption, and one in which the reducing species reacts with and removes the adsorbed oxygen, thereby lowering the workfunction, when the oxidizing and reducing species in the gas phase are at or rich of stoichiometry.

3. A sensing structure as recited in claim 2 in which said active surface material is a platinum-ceramic composite.

4. A sensing structure as recited in claim 2 further comprising a heater located adjacent said active surface for heating said active surface to a predetermined temperature.

5. A sensing structure as recited in claim 1 wherein said capacitive device includes a chemically inactive surface placed in proximity to said active surface to form a capacitor with said active surface.

6. A sensing structure as recited in claim 5 wherein said inactive surface is made of gold.

7. A sensing structure as recited in claim 1 for sensing a wide range of air-to-fuel ratio about the stoichiometric value where the active surface is simultaneously a working electrode of a solid electrochemical cell for electrochemically pumping oxygen gas to or from the working electrode with respect to a reference electrode that is exposed to a reference gas containing oxygen.

8. A sensing structure as recited in claim 7 in which the working electrode is simultaneously one in which the pumping of oxygen to or from that surface causes the workfunction of that surface to increase or decrease respectively in an amount comparable to or in excess of that change which is caused by varying the oxidizing and reducing species in the gas phase about their stoichiometric concentrations.

9. A sensing structure as recited in claim 7 in which said working electrode is platinum.

10. A sensing structure as recited in claim 7 in which said working electrode is a platinum-ceramic composite.

11. A sensing structure as recited in claim 1 further comprising a current detecting means for determining current flow in said capacitive device.

12. A sensing structure as recited in claim 1 further including current detecting means coupled between said plates.

13. A method of sensing a stoichiometric ratio of an oxidizing and reducing species in an ambient gas phase including the steps of:
   providing an active surface which interacts with the gas phase and has a workfunction which changes value at the stoichiometric ratio;
   providing an inactive surface which in combination with the active surface forms a capacitive device that produces an electrical signal that is proportional to the change in workfunction;
   connecting an ammeter between the active and inactive surfaces to sense a current flowing between those surfaces when concentrations of the oxidizing and reducing species active constituents of the gas phase are varied about the stoichiometric ratio; and
   coupling an integrating circuit to the ammeter to provide an output signal proportional to a total electric charge transferred between the two surfaces such that two distinct levels of output from the integrating circuit correspond to gas phase conditions either rich or lean of stoichiometry and a point intermediate between these two levels corresponding to and thereby sensing the stoichiometric condition in the gas phase.

14. A method of sensing the stoichiometric ratio of an oxidizing and reducing species in an ambient gas phase as recited in claim 13 further including the steps of:

providing an electrochemical cell adjacent the active surface for pumping oxygen;

providing a negative feedback circuit having a feedback impedance and an output;

coupling the output of the negative feedback circuit to the electrochemical cell in a manner to effect pumping of oxygen to or from the active surface;

applying step-like outputs from the capacitive device to a negative input of a feedback amplifier while a fixed voltage is applied to a positive input corresponding to an intermediate value in the step-like outputs;

arranging the feedback impedance of the feedback circuit so that an output current of the feedback circuit will cause sufficient oxygen to be pumped to the active surface so that the workfunction of that surface, as a combined result of oxygen pumping and gas phase interactions on the workfunction, will be held at an intermediate value between its rich and lean extremes, despite variations in the composition of the active constituents in the gas phase, an output of the capacitive device in this condition being close to a voltage applied to the positive input of the feedback amplifier; and determining the current supplied by the feedback circuit to the electrochemical cell being proportional to and thereby sensing an air-to-fuel ratio.

15. A method of sensing a stoichiometric ratio of an oxidizing and reducing species in an ambient gas phase including the steps of:

providing an active surface which interacts with the gas phase and has a workfunction which changes value at the stoichiometric ratio;

providing an inactive surface which in combination with the active surface forms a capacitive device that produces an electrical signal that is proportional to the change in workfunction;

vibrating the active and inactive surfaces with respect to each other thereby changing their mutual capacitance;

connecting an alternating current sensing device between the active and inactive surfaces to measure an alternating current flow between the surfaces due to the vibration and changes in the magnitude of the alternating current flow due to change in concentrations of the ambient gas phase constituents;

coupling a demodulating circuit to an output of an ammeter which yields two distinct output levels corresponding to gas phase conditions rich or lean of stoichiometry respectively with a point intermediate between these two levels corresponding to an thereby sensing a stoichiometric condition in the gas phase.

16. A method of sensing the stoichiometric ratio of an oxidizing and reducing species in an ambient gas phase as recited in claim 15 further including the steps of:

providing an electrochemical cell adjacent to the active surface for pumping oxygen;

coupling an output of a negative feedback circuit to an electrochemical cell in a manner to effect the pumping of oxygen to or from the active surface;

applying step-like outputs from the capacitive device to a negative input of a feedback amplifier while a fixed voltage is applied to a positive input corresponding to an intermediate value in the step-like outputs;

arranging the feedback impedance of the feedback circuit so that an output current of the feedback circuit will cause sufficient oxygen to be pumped to the active surface so that the workfunction of the surface, as a combined result of oxygen pumping and gas phase interactions on the workfunction, will be held at an intermediate value between its rich and lean extremes, despite variations in composition of active constituents in the ambient gas phase, the output of the capacitive device in this condition being close to a voltage applied to a positive input of the feedback amplifier; and determined a current supplied by the feedback circuit to the electrochemical cell being proportional to and thereby sensing an air-to-fuel ratio.

* * * * *